United States Patent [19]
Wächtler et al.

[11] Patent Number: 4,719,032
[45] Date of Patent: Jan. 12, 1988

[54] CYCLOHEXANE DERIVATIVES

[75] Inventors: Andreas Wächtler, Griesheim; Joachim Krause, Dieburg; Reinhard Hittich, Modautal; Bernhard Scheuble, Alsbach, all of Fed. Rep. of Germany

[73] Assignee: Merck Patent Gesellschaft mit beschrankter Haftung, Darmstadt, Fed. Rep. of Germany

[21] Appl. No.: 842,692

[22] Filed: Mar. 21, 1986

[30] Foreign Application Priority Data

Mar. 22, 1985 [DE] Fed. Rep. of Germany ....... 3510312

[51] Int. Cl.$^4$ .................... C09K 19/34; G02F 1/13; C07C 43/184; C07C 69/013
[52] U.S. Cl. ..................... 252/299.63; 252/299.5; 350/350 R; 350/350 S; 560/1; 560/116; 560/118; 560/179; 560/183; 560/185; 560/186; 560/187; 560/188; 568/367; 568/591; 568/606; 568/622; 568/623; 568/624; 568/625; 568/664
[58] Field of Search .............. 252/299.5, 299.63; 350/350 R, 350 S; 560/116, 118, 179, 183, 185, 186, 187, 188, 1; 568/367, 591, 606, 622, 623, 664, 624, 625

[56] References Cited

U.S. PATENT DOCUMENTS

| | | |
|---|---|---|
| 4,257,078 | 11/1982 | Carr et al. ................. 252/299.63 |
| 4,361,494 | 11/1982 | Osman et al. .............. 252/299.63 |
| 4,419,263 | 12/1983 | Praefcke et al. ........... 252/299.63 |
| 4,431,853 | 2/1984 | Sato et al. ................. 252/299.63 |
| 4,439,015 | 3/1984 | Rich et al. ................. 252/299.63 |
| 4,510,069 | 4/1985 | Eidenschink et al. ..... 252/299.63 |
| 4,556,745 | 12/1985 | Carr et al. ................. 252/299.63 |
| 4,558,151 | 12/1985 | Takatsu et al. ............ 252/299.63 |
| 4,564,694 | 1/1986 | Hirai et al. ................. 252/299.63 |
| 4,565,425 | 1/1986 | Petrzilka et al. .......... 252/299.63 |
| 4,606,845 | 8/1986 | Romer et al. .............. 252/299.63 |
| 4,610,805 | 9/1986 | Schellenberger et al. ...... 252/299.63 |
| 4,617,140 | 10/1986 | Eidenschink et al. ......... 252/299.63 |
| 4,621,901 | 11/1986 | Petrzilka et al. ............ 252/299.63 |
| 4,622,164 | 11/1986 | Eidenschink et al. ......... 252/299.63 |
| 4,659,502 | 4/1987 | Fearon et al. ................ 252/299.5 |

FOREIGN PATENT DOCUMENTS

| | | | |
|---|---|---|---|
| 129177 | 12/1984 | European Pat. Off. ....... | 252/299.67 |
| 57-118526 | 7/1982 | Japan ............................. | 252/299.63 |
| 2092169 | 8/1982 | United Kingdom .......... | 252/299.63 |

OTHER PUBLICATIONS

Osman, M., Mol. Cryst. Liq. Cryst., vol. 72 (Letters), pp. 291-295 (1982).
Osman, M., Mol. Cryst. Liq. Cryst., vol. 82 (Letters), pp. 47-52 (1982).

*Primary Examiner*—Teddy S. Gron
*Attorney, Agent, or Firm*—Millen & White

[57] ABSTRACT

Cyclohexane derivatives of formula I

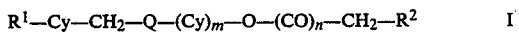

$$R^1\text{—Cy—CH}_2\text{—Q—(Cy)}_m\text{—O—(CO)}_n\text{—CH}_2\text{—R}^2 \quad \text{I}$$

where
$R^1$ denotes alkyl with 1 to 12 C atoms in which also one or two non-adjacent $CH_2$ groups may be replaced by —O—, —CO—, —O—CO—, —CO—O— or —CH=CH—,
$R^2$ denotes H, alkyl with 1 to 12 C atoms in which also one or two non-adjacent $CH_2$ groups may be replaced by —O—, —CO—, —O—CO— or —CO—O—,
Cy denotes trans-1,4-cyclohexylene
Q denotes —$CH_2$— or —O—,
m denotes 1 or 2, and
n denotes 0 or 1,
are suitable as components of liquid-crystalline phases.

17 Claims, No Drawings

CYCLOHEXANE DERIVATIVES

This invention relates to new cyclohexane derivatives.

SUMMARY OF THE INVENTION

It is an object of this invention to provide new stable liquid-crystalline or mesogenic compounds which are suitable as components of liquid-crystalline dielectrics.

Upon further study of the specification and appended claims, further object and advantages of this invention will become apparent to those skilled in the art.

These objects have been achieved by providing new cyclohexane derivatives of formula I

$$R^1-Cy-CH_2-Q-(Cy)_m-O-(CO)_n-CH_2-R^2$$

where $R^1$ denotes alkyl with 1 to 12C atoms in which also one or two non-adjacent $CH_2$ groups may be replaced by —O—, —CO—, —O—CO—, —CO—O— or —CH=CH—, $R^2$ denotes H, alkyl with 1 to 12C atoms in which also one or two non-adjacent $CH_2$ groups may be replaced by —O—, —CO—, —O—CO— or —CO—O—, cy denotes 1,4 -cyclohexylene (especially in trans configuration), Q denotes —$CH_2$— or —O—m denotes 1 or 2, and n denotes 0 or 1.

Like similar compounds known, for example, from German OffenLegungsschrift No. 3,321,373, the compounds of formula I can be used as components of Liquid-crystalline phases, especially for displays which are based on the principle of the twisted cell, the quest-host effect, the effect of the deformation of aligned phases or the dynamic scattering effect.

It was found that the compounds of formula I are excellently suitable as components of Liquid-crystalline dielectrics. In particular, using them stable Liquid-crystalline phases with relatively low optical anisotropy, with considerable nematic character and particularly low viscosity can be prepared which are distinguished in electrooptical display elements based on the principle of the twisted cell and/or the guest-host effect by a particularly beneficial angular dependence of the contrast.

In addition to the provision of compounds of formula I, the range of Liquid-crystalline substances which are suitable for the manufacture of nematic mixtures from various applicational points of view is quite generally considerably extended.

The compounds of formula I have a wide field of application. Depending on the choice of the substituents these compounds may be used as basic materials of which Liquid-crystalline phases are predominantly composed; however, compounds of formula I can also be added to Liquid-crystalline basic materials from other classes of compound in order to influence, for example, the angular dependence of the contrast and/or the optical anisotropy and/or the viscosity of such a phase.

The compounds of formula I are furthermore suitable as intermediate products for the manufacture of other substances which can be used as components of Liquid-crystalline phases.

The compounds of formula I are colorless in the pure state and form Liquid-crystalline mesophases in a temperature range beneficially disposed for electrooptical use. They are very stable chemically, thermally and towards light.

The subject of the invention is therefore the compounds of formula I and also a process for their preparation, characterized in that corresponding cyclohexanols or their reactive derivatives are etherified or esterified.

In addition a subject of the invention is the use of the compounds of formula I as components of Liquid-crystalline phases. A subject of the invention is furthermore Liquid-crystalline phases with a content of at least one compound of formula I and also Liquid-crystalline display elements, in particular electrooptical display elements which contain phases of this type.

DETAILED DISCUSSION

In the compounds of formula I those stereoisomers are preferred in which all the 1,4-cyclohexylene groups are trans-substituted in the 1,4 position.

In the compounds of the formulae above and below the alkyl radicals $R^1$ or $R^2$, in which also one ("alkoxy" or "oxaalkyl") or two ("alkoxyalkoxy" or "dioxaalkyl") non-adjacent $CH_2$ groups may be replaced by C atoms, may be straight-chain or branched. Preferably they are straight-chain, have 2, 3, 4, 5, 6, 7, 8, 9 or 10C atoms and consequently preferably denote ethyl, propyl, butyl, pentyl, hexyl, heptyl, octyl, nonyl, decyl, ethoxy, propoxy, butoxy, pentoxy, hexoxy, heptoxy, octoxy, nonoxy, decoxy, 2-oxapropyl (=methoxymethyl), 2- (=ethoxymethyl) or 3-oxabutyl (=2-methoxymethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8-or 9-oxadecyl, and furthermore methyl, undecyl, dodecyl, methoxy, undecoxy, dodecoxy, 2-, 3-, 4-, 5-, 6-, 7-, 8-, 9- or 10-oxaundecyl, 2-, 3-, 4-, 5-, 6-, 7-, 8-, 9-, 10- or 11-oxadodecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,3-, 1,4-, 1,5-, 1,6-, 1,7-, 2,4-, 2,5-, 2,6-, 2,7-, 3,5-, 3,6-, 3,7-, 4,6-, 4,7- or 5,7-dioxaoctyl, 1,3-, 1,4-, 1,5-, 1,6-, 1,7-, 1,8-, 2,4-, 2,5-, 2,6-, 2,7-, 2,8-, 3,5-, 3,6-, 3,7-, 3,8-, 4,6-, 4,7-, 4,8-, 5,7- or 5,8-dioxanonyl, 1,3-, 1,4-, 1,5-, 1,6-, 1,7-, 1,8-, 1,9-, 2,4-, 2,5-, 2,6-, 2,7-, 2,8-, 2,9-, 3,5-, 3,6-, 3,7-, 3,8-, 3,9-, 4,6-, 4,7-, 4,8-, 4,9-, 5,7-, 5,8- or 5,9-dioxadecyl. $R^1$ and $R^2$ are in each case preferably alkyl or alkoxy, in particular n-alkyl. Q is preferably $CH_2$.

Compounds of formula I with branched wing groups $R^1$ or $R^2$ are occasionally of importance because of a better solubility in the usual Liquid-crystalline basic materials, in particular, however, as chiral doping substances if they are optically active. Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-methylpentyl.

Among the compounds of formula I those compounds are preferred in which at least one of the radicals contained therein has one of the preferred meanings specified.

Particularly preferred compounds of formula I correspond to the formulae Ia to Ig:

| | |
|---|---|
| n—alkyl—Cy—CH$_2$CH$_2$—Cy—n—alkoxy | Ia |
| n—alkyl—Cy—CH$_2$CH$_2$—Cy—n—alkanoyloxy | Ib |
| n—alkyl—Cy—CH$_2$CH$_2$—Cy—Cy—n—alkoxy | Ic |
| n—alkyl—Cy—CH$_2$CH$_2$—Cy—Cy—n—alkanoyloxy | Id |
| n—alkyl—Cy—CH$_2$O—Cy—Cy—n—alkoxy | Ie |
| n—alkyl—Cy—CH$_2$O—Cy—Cy—n—alkanoyloxy | If |
| n—alkyl—Cy—CH$_2$O—Cy—n—alkoxy | Ig | where the n-alkyl, n-alkoxy or n-alkanoyloxy groups in each case preferably contain 2 to 8C atoms.

The compounds of the formula I may be prepared by methods known per se as they are described in the literature (e.g. in the standard works such as Houben-Weyl, Methoden der Organischen Chemie (Methods of Organic Chemistry), Georg-Thieme-Verlag, Stuttgart), and in fact under the reaction conditions which are known and suitable for the said reactions. In this connection use can also be made of variations known per se not mentioned in more detail here.

The starting substance may, if desired, also be formed in situ in a manner such that they are not separated from the reaction mixture, but are immediately reacted further to the compounds of formula I. As starting substances the corresponding cyclohexanols of formula II are preferably used,

$$R^1\text{-Cy-CH}_2\text{-Q-(Cy)}_m\text{-OH} \qquad \text{II}$$

where $R^1$, Q, Cy and m have the specified meaning.

The compounds of formula II may, for example, be obtained by methods known per se by etherification of trans-4-$R^1$-1-bromomethylcyclohexane with trans-1,4-cyclohexanediol or trans, trans-4,4'bicyclohexanediol (Q=—O—) or by hydrogenation of corresponding phenol derivatives of formula III,

$$R^1\text{-Cy-CH}_2\text{CH}_2\text{-(Phe)}_m\text{-OH} \qquad \text{III}$$

where $R^1$, Cy and m have the specified meaning and Phe is 1,4-phenylene.

The phenol derivatives of formula III are, for example, obtainable by Fries rearrangement from the corresponding phenol esters (m=1) or by boiling down corresponding diazonium salts (m=1 or 2) with phenol. The corresponding amines are accessible by Hofmann degradation of the corresponding acid amides which are in turn obtainable from the cyano compounds described in German Offenlegungsschrift No. 2,922,236.

The phenol derivatives of formula III can furthermore be prepared by Friedel-Crafts acylation of anisole with 2-(trans-4-$R^1$-cyclohexyl)-acetyl halide (e.g. with SnCl$_4$ as described by P. H. Hey et al., J. Chem. Soc. 1949, page 3156), a reduction of the ketone obtained and subsequent ether cleavage.

In addition to the corresponding free cyclohexanols their reactive derivatives are also suitable.

As reactive derivatives of the said alcohols, in particular the corresponding metal alcoholates in which M denotes one equivalent of a metal, preferably an alkali metal such as Na or K, are suitable.

To prepare esters of formula I (n=1), a corresponding cyclohexanol of formula II or one of its reactive derivatives is preferably reacted with a corresponding carboxylic acid or one its reactive derivatives.

As reactive derivatives of the said carboxylic acids the acid halides are, in particular, suitable, especially the chlorides and bromides, and furthermore the anhydrides, azides or esters, in particular alkyl esters with 1-4C atoms in the alkyl group.

The esterification is advantageously carried out in the presence of an inert solvent. Well suited are, in particular, ethers such as diethyl ether, di-n-butyl ether, THF, dioxane or anisole, ketones such as acetone, butanone or cyclohexanone, amides such as DMF or phosphoryl hexmethyl triamide, hydrocarbons such as benzene, toluene or xylol, halogenated hydrocarbons such as carbon tetrachloride or tetrachloroethylene and sulphoxides such as dimethyl sulphoxide or sulpholane. Solvents immiscible with water may at the time be advantageously used for the azeotropic distilling of the water formed in the esterification.

Occasionally an excess of an organic base i.g. pyridine, quinoline or triethylamine can also be used as solvent for the esterification. The esterification can also be carried out in the absence of a solvent, e.g. by simply heating the components in the presence of sodium acetate. The reaction temperature is usually between −50° and +250°, preferably between −20° and +80°. At these temperatures the esterification reaction is complete as a rule after 15 minutes to 48 hours.

In detail the reaction conditions for the esterification essentially depend on the nature of the starting substances used. Thus, a free carboxylic acid is reacted with a free alcohol as a rule in the presence of a strong acid, for example a mineral acid such as hydrochloric or sulphuric acid. A preferred mode of reaction is the reaction of an acid anhydride or, in particular, of an acid chloride with an alcohol, preferably in a basic medium, in particular alkali metal hydroxides such as sodium or potassium hydroxide, alkali metal carbonates or hydrogen carbonates such as sodium carbonate, sodium hydrogen carbonate, potassium carbonate or potassium hydrogen carbonate, alkalimetal acetates such as sodium or potassium acetate, alkaline earth metal hydroxides such as calcium hydroxide or organic bases such a triethylamine, pyridine, lutidine, collidine or quinoline being of importance as bases. Another preferred type of esterification consists in first converting the alcohol into the sodium or potassium alcoholate, e.g. by treatment with ethanolic sodium or potassium hydroxide, isolating the alcoholate and suspending it together with sodium hydrogen carbonate or potassium carbonate with stirring in acetone of diethyl ether and mixing this suspension with a solution of the acid chloride or anhydride in diethyl ether, acetone or DMF, expediently at temperatures between about −25° and +25° C.

To prepare the ethers of formula I (n=0), preferably a corresponding cyclohexanol of formula II or one of its reactive derivatives is reacted with a corresponding alkyl halide, sulphonate or dialkyl sulphate, expediently in an inert solvent such as acetone, 1,2-dimethoxyethane, DMF or dimethyl sulphoxide or also an excess of aqueous or aqueous/alcolic NaOH or KOH at temperatures between about 20° and 100°.

Expediently, the hydroxy compound is first converted into a corresponding metal derivative, e.g. by treatment with NaH, NaNH$_2$, NaOH, KOH, Na$_2$CO$_3$ or K$_2$CO$_3$ into the corresponding alkali metal alcoholate.

The dielectrics according to the invention comprise 2 to 25, preferably 3 to 15 components, including at least one compound of formula I. The other components are preferably selected from the nematic of nematogeneous substances, in particular the known substances from the classes of the azoxybenzenes, benylanilines, biphenyls, terphenyls, phenyl- or cyclohexylbenzoates, phenyl or cyclohexyl cyclohexanecarboxylate, phenylcyclohexanes, cyclobiphenyls, cyclohexylcyclohexanes, cyclohexylnaphthalenes, 1,4-bisyclohexylbenzenes, 4,4'-biscyclohexylbiphenyls, phenyl- or cyclohexylpyrimidine, phenyl-, or cyclohexyldioxanes, phenyl- or cyclohexyldithianes, 1,2-bisphenylethanes, 1,2-biscyclohexylethanes, 1-cyclohexyl-2-phenylethanes, optionally halogenated stilbenes, benzyl phenyl ether, tolanes and substituted cinnamic acids.

The most important compounds suitable as components of Liquid-crystalline dielectrics of this type may be characterized by the formula IV

R'-L-G-E-R"      IV where L and E each denote a carbo- or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, it being possible for the 1,4-disubstituted cyclohexane rings additionally to carry a cyano group in the 1 or 4 position,

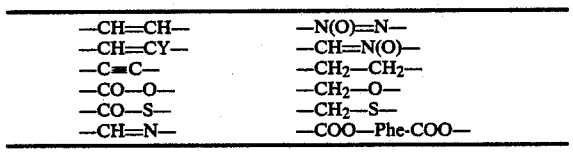

or a single C—C bond, Y denotes halogen, preferably chlorine, or —CN, and R' and R" denote alkyl, alkoxy, alkanoyloxy or alkoxycarbonyloxy with up to 18, preferably up to 8 carbon atoms or one of these radicals also denotes CN, NC, NO$_2$, CF$_3$, C, Cl.

In most of these compounds R' and R" are different from each other, one of these radicals usually being an alkyl or alkoxy group. However, other variations of the substituents provided are common. Many such substances or also mixtures thereof are obtainable commercially. All these substances can be prepared by methods known from the literature.

The dielectrics according to the invention contain as a rule at least 30, preferably 50–99, in particular 60–98 percent by weight of the compounds of formulae I and IV. Of this amount preferably at least 6 percent by weight, usually even 10–40 percent by weight, is allotted to one or more compounds of formula I. However, the invention encompasses also those liquid-crystalline dielectrics to which, for example, only less than 5 percent by weight to 0.1 to 3 percent by weight of one or more compounds of formula I has been added for doping purposes.

The preparation of the dielectrics according to the invention are carried out in a manner usual per se. As a rule, the components are dissolved in each other, expediently at elevated temperature. The liquid-crystalline dielectrics according to the invention can be modified by suitable additive in a manner such that they can be used in all the types of liquid-crystal display elements which have hitherto become known.

Additives of this type are known to those skilled in the art and described comprehensively in the literature. For example conducting salts, preferably ethyldimethyldodecylammonium 4-hexyloxybenzoate, tetrabutylammonium tetraphenyl boranate or complex salts of crown ethers (cf. e.g. I. Haller et al., Mol. Cryst. Liq. Cryst., Volume 24, pages 249–258 (1973)) can be added to improve the conductivity, dichroic dyestuffs to prepare coloured quest-host systems or substances to modify the dielectric anisotropy, the viscosity and/or the orientation of the nematic phase. Such substances are described, for example in the German Offenlegungsschriften Nos. 2,209,127, 2,240,864, 2,321,632, 2,338,281, 2,450,088, 2,637,430, 2,853,728 and 2,902,117.

Without further elaboration, it is believed that one skilled in the art can, using the preceding description, utilize the present invention to its fullest extent. The following preferred specific embodiment are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

"Usual working-up" means that water is added, extraction is carried out with methylene chloride, separation is carried out, the organic phase is dried and concentrated by evaporation, and the product is purified by crystallization and/or chromatography.

EXAMPLE 1

2.0 g of butyryl chloride are added to a solution of 3.3 g of trans, trans-4'-[2-(trans-4-n-propylcyclohexyl)-ethyl]bicyclohexane-4-ol in 200 ml of pyridine, the mixture is stirred overnight and then 700 ml of toluene is added. The toluene phase is washed successively with hydrochloric acid, NaOH solution and water and dried with Na$_2$SO$_4$. The residue left after the evaporation of the toluene is recrystallized from acetone. Trans,trans-4'-[2-(trans-4-n-propylcyclohexyl)ethyl]-4-butyryloxybicyclohexane is obtained. The following are prepared in a similar manner:

trans,trans-4'-[2-(trans-4-propylcyclohexyl)ethyl]-4-acetoxybicyclohexane trans,trans-4'-[2-(trans-4-propylcyclohexyl)ethyl]-4-propionyloxybicyclohexane trans,trans-4'-[2-(trans-4-propylcyclohexyl)ethyl]-4-pentanoyloxybicyclohexane trans,trans-4'-[2-(trans-4-ethylcyclohexyl)ethyl]-4-acetoxybicyclohexane trans,trans-4'-[2-(trans-4-ethylcyclohexyl)ethyl]-4-propionyloxybicyclohexane trans,trans-4'-[2-(trans-4-ethylcyclohexyl)ethyl]-4-butyryloxybicyclohexane trans,trans-4'-[2-(trans-4-ethylcyclohexyl)ethyl]-4pentanoyloxybicyclohexane trans,trans-4'-[2-(trans-4-butylcyclohexyl)ethyl]-4acetoxybicyclohexane trans,trans-4'-[2-(trans-4-butylcyclohexyl)ethyl]-4-propionyloxybicyclohexane trans,trans-4'-[2-(trans-4-butylcyclohexyl)ethyl]-4-butyryloxybicyclohexane trans,trans-4'-[2-(trans-4-butylcyclohexyl)ethyl]-4-pentanoyloxybicyclohexane trans,trans-4'-[2-(trans-4-pentylcyclohexyl)ethyl]-4-acetoxybicyclohexane
trans,trans-4'-[2-(trans-4-pentylcyclohexyl)ethyl]-4-propionyloxybicyclohexane
trans,trans-4'-[2-(trans-4-pentylcyclohexyl)ethyl]4-butyryloxybicyclohexane
trans,trans-4'-[2-(trans-4-pentylcyclohexyl)ethyl]-4-pentanoyloxybicyclohexane
trans,trans-4'-[2-(trans-4-heptylcyclohexyl)ethyl]-4-acetoxybicyclohexane
trans,trans-4'-[2-(trans-4-heptylcyclohexyl)ethyl]-4-propionyloxybicyclohexane
trans,trans-4'-[2-(trans-4-heptylcyclohexyl)ethyl]-4-butyryloxybicyclohexane
trans,trans-4'-[2-(trans-4-heptylcyclohexyl)ethyl]-4-pentanoyloxybicyclohexane
trans-4-[2-(trans-4-ethylcyclohexyl)ethyl]acetoxycyclohexane
trans-4-[2-(trans-4-ethylcyclohexyl)ethyl]propionyloxycyclohexane
trans-4-[2-(trans-4-ethylcyclohexyl)ethyl]butyryloxycyclohexane
trans-4-[2-(trans-4-ethylcyclohexyl)ethyl]pentanoyloxycyclohexane
trans-4-[2-(trans-4-propylcyclohexyl)ethyl]acetoxycyclohexane
trans-4-[2-(trans-4-propylcyclohexyl)ethyl]propionyloxycyclohexane
trans-4-[2-(trans-4-propylcyclhoexyl)ethyl]butyryloxycyclohexane, mp 25°, cp 73°
trans-4-[2-(trans-4-propylcyclohexyl)ethyl]pentanoyloxycyclohexane
trans-4-[2-(trans-4-butylcyclohexyl)ethyl]acetoxycyclohexane
trans-4-[2-(trans-4-butylcyclohexyl)ethyl]propionyloxycyclohexane
trans-4-[2-(trans-4-butylcyclohexyl)ethyl]butyryloxycyclohexane
trans-4-[2-(trans-4-butylcyclohexyl)ethyl]pentanoyloxycyclohexane
trans-4-[2-(trans-4-pentylcyclohexyl)ethyl]acetoxycyclohexane
trans-4-[2-(trans-4-pentylcyclohexyl)ethyl]propionyloxycyclohexane
trans-4-[2-(trans-4-pentylcyclohexyl)ethyl]butyryloxycyclohexane
trans-4-[2-(trans-4-pentylcyclohexyl)ethyl]pentanoyloxycyclohexane
trans-4-[2-(trans-4-heptylcyclohexyl)ethyl]acetoxycyclohexane
trans-4-[2-(trans-4-heptylcyclohexyl)ethyl]propionyloxycyclohexane
trans-4-[2-(trans-4-heptylcyclohexyl)ethyl]butyryloxycyclohexane
trans-4-[2-(trans-4-heptylcyclohexyl)ethyl]pentanoyloxycyclohexane

EXAMPLE 2

0.5 g of 35% KH dispersion is added to a solution of 0.9 g of trans-4-[2-(trans-4-n-propylcyclohexyl)ethyl]-cyclohexanol in 250 ml of THF and stirring is carried out for two hours under reflux. Then 0.6 g of n-iodobutane is added and stirring is carried out for two hours at room temperature. Excess potassium hydride is destroyed with water. Extraction is carried out with methylene chloride, drying is carried with Na$_2$SO$_4$ and the solvent evaporated off. The residue left behind is worked up chromatographically. 1-(trans-4-n-butoxycyclohexyl)-2-(trans-4-n-propylcyclohexyl)ethane is obtained.

The following are prepared analogously:
1-(trans-4-butoxycyclohexyl)-2-(trans-4-ethylcyclohexyl)ethane
1-(trans-4-butoxycyclohexyl)-2-(trans-4-butylcyclohexyl)ethane
1-(trans-4-butoxycyclohexyl)-2-(trans-4-pentylcyclohexyl)ethane
1-(trans-4-butoxycyclohexyl)-2-(trans-4-heptylcyclohexyl)ethane
1-(trans-4-hexoxycyclohexyl)-2-(trans-4-ethylcyclohexyl)ethane
1-(trans-4-hexoxycyclohexyl)-2-(trans-4-propylcyclohexyl)ethane
1-(trans-4-hexoxycyclohexyl)-2-(trans-4-butylcyclohexyl)ethane
1-(trans-4-hexoxycyclohexyl)-2-(trans-4-pentylcyclohexyl)ethane
1-(trans-4-hexoxycyclohexyl)-2-(trans-4-hexylcyclohexyl)ethane
1-(trans-4-hexoxycyclohexyl)-2-(trans-4-heptylcyclohexyl)ethane
1-(trans-4-propoxycyclohexyl)-2-(trans-4-ethylcyclohexyl)ethane
1-(trans-4-propoxycyclohexyl)-2-(trans-4-propylcyclohexyl)ethane
1-(trans-4-propoxycyclohexyl)-2-(trans-4-butylcyclohexyl)ethane
1-(trans-4-propoxycyclohexyl)-2-(trans-4-pentylcyclohexyl)ethane
1-(trans-4-propoxycyclohexyl)-2-(trans-4-hexylcyclohexyl)ethane
1-(trans-4-propoxycyclohexyl)-2-(trans-4-heptylcyclohexyl)ethane
1-(trans-4-ethoxycyclohexyl)-2-(trans-4-ethylcyclohexyl)ethane
1-(trans-4-ethoxycyclohexyl)-2-(trans-4-propylcyclohexyl)ethane
1-(trans-4-ethoxycyclohexyl)-2-(trans-4-butylcyclohexyl)ethane
1-(trans-4-ethoxycyclohexyl)-2-(trans-4-pentylcyclohexyl)ethane
1-(trans-4-ethoxycyclohexyl)-2-(trans-4-hexylcyclohexyl)ethane
1-(trans-4-ethoxycyclohexyl)-2-(trans-4-heptylcyclohexyl)ethane
1-(trans-4-methoxycyclohexyl)-2-(trans-4-ethylcyclohexyl)ethane
1-(trans-4-methoxycyclohexyl)-2-(trans-4-propylcyclohexyl)ethane, mp 14°, cp 22°
1-(trans-4-methoxycyclohexyl)-2-(trans-4-butylcyclohexyl)ethane
1-(trans-4-methoxycyclohexyl)-2-(trans-4-pentylcyclohexyl)ethane, mp 13°, cp 47°
1-(trans-4-methoxycyclohexyl)-2-(trans-4-hexylcyclohexyl)ethane
1-(trans-4-methoxycyclohexyl)-2-(trans-4-heptylcyclohexyl)ethane
1-(trans,trans-4'-butoxybicyclohex-4-yl)-2-(trans-4-ethylcyclohexyl)ethane
1-(trans,trans-4'-butoxybicyclohex-4-yl)-2-(trans-4-propylcyclohexyl)ethane
1-(trans,trans-4'-butoxybicyclohex-4-yl)-2-(trans-4-butylcyclohexyl)ethane
1-(trans,trans-4'-butoxybicyclohex-4-yl)-2-(trans-4-pentylcyclohexyl)ethane 1-(trans,trans-4'-butoxybicyclohex-4-yl)-2-(trans-4-hexylcyclohexyl)ethane
1-(trans,trans-4'-butoxybicyclohex-4-yl)-2-(trans-4-heptylcyclohexyl)ethane
1-(trans,trans-4'-propoxybicyclohex-4-yl)-2-(trans-4-ethylcyclohexyl)ethane
1-(trans,trans-4'-propoxybicyclohex-4-yl)-2-(trans-4-propylcyclohexyl)ethane
1-(trans,trans-4'-propoxybicyclohex-4-yl)-2-(trans-4-butylcyclohexyl)ethane
1-(trans,trans-4'-propoxybicyclohex-4-yl)-2-(trans-4-pentylcyclohexyl)ethane
1-(trans,trans-4'-propoxybicyclohex-4-yl)-2-(trans-4-hexylcyclohexyl)ethane
1-(trans,trans-4'-propoxybicyclohex-4-yl)-2-(trans-4-heptylcyclohexyl)ethane
1-(trans,trans-4'-ethoxybicyclohex-4-yl)-2-(trans-4-ethylcyclohexyl)ethane
1-(trans,trans-4'-ethoxybicyclohex-4-yl)-2-(trans-4-propylcyclohexyl)ethane
1-(trans,trans-4'-ethoxybicyclohex-4-yl)-2-(trans-4-butylcyclohexyl)ethane
1-(trans,trans-4'-ethoxybicyclohex-4-yl)-2-(trans-4-pentylcyclohexyl)ethane
1-(trans,trans-4'-ethoxybicyclohex-4-yl)-2-(trans-4-hexylcyclohexyl)ethane
1-(trans,trans-4'-ethoxybicyclohex-4-yl)-2-(trans-4-heptylcyclohexyl)ethane
1-(trans,trans-4'-methoxybicyclohex-4-yl)-2-(trans-4-ethylcyclohexyl)ethane
1-(trans,trans-4'-methoxybicyclohex-4-yl)-2-(trans-4-propylcyclohexyl)ethane
1-(trans,trans-4'-methoxybicyclohex-4-yl)-2-(trans-4-butylcyclohexyl)ethane
1-(trans,trans-4'-methoxybicyclohex-4-yl)-2-(trans-4-pentylcyclohexyl)ethane
1-(trans,trans-4'-methoxybicyclohex-4-yl)-2-(trans-4-hexylcyclohexyl)ethane
1-(trans,trans-4'-methoxybicyclohex-4-yl)-2-(trans-4-heptylcyclohexyl)ethane

EXAMPLE 3

A mixture of 1.56 g of NaH in 30 ml of THF is mixed with 9.4 g of 4-ethoxycyclohexanol and stirred for 8 hours. A solution of 16 g of trans-4-bromomethyl-1-n-pentylcyclohexane in 20 ml of THF is slowly added dropwise, boiling is carried out for 2 hours and working-up done in the usual manner. Trans-4-ethoxycyclohexyl-trans-4-n-pentylcyclohexyl methyl ether is obtained.

The following are prepared analogously:
trans-4-ethoxycyclohexyl-trans-4-ethylcyclohexyl methyl ether
trans-4-ethoxycyclohexyl-trans-4-propylcyclohexyl methyl ether
trans-4-ethoxycyclohexyl-trans-4-butylcyclohexyl methyl ether
trans-4-ethoxycyclohexyl-trans-4-heptylcyclohexyl methyl ether
trans-4-methoxycyclohexyl-trans-4-ethylcyclohexyl methyl ether
trans-4-methoxycyclohexyl-trans-4-propylcyclohexyl methyl ether
trans-4-methoxycyclohexyl-trans-4-butylcyclohexyl methyl ether
trans-4-methoxycyclohexyl-trans-4-pentylcyclohexyl methyl ether
trans-4-methoxycyclohexyl-trans-4-heptylcyclohexyl methyl ether
trans-4-propoxycyclohexyl-trans-4-ethylcyclohexyl methyl ether
trans-4-propoxycyclohexyl-trans-4-propylcyclohexyl methyl ether
trans-4-propoxycyclohexyl-trans-4-butylcyclohexyl methyl ether
trans-4-propoxycyclohexyl-trans-4-pentylcyclohexyl methyl ether
trans-4-propoxycyclohexyl-trans-4-heptylcyclohexyl methyl ether
trans-4-butoxycyclohexyl-trans-4-ethylcyclohexyl methyl ether
trans-4-butoxycyclohexyl-trans-4-propylcyclohexyl methyl ether
trans-4-butoxycyclohexyl-trans-4-butylcyclohexyl methyl ether
trans-4-butoxycyclohexyl-trans-4-pentylcyclohexyl methyl ether
trans-4-butoxycyclohexyl-trans-4-heptylcyclohexyl methyl ether
trans-trans-4'-ethoxybicyclohex-4-yl-trans-4-ethylcyclohexyl methyl ether
trans-trans-4'-ethoxybicyclohex-4-yl-trans-4-propylcyclohexyl methyl ether
trans-trans-4'-ethoxybicyclohex-4-yl-trans-4-butylcyclohexyl methyl ether trans-trans-4'-ethoxybicyclohex-4-yl-trans-4-pentylcyclohexyl methy ether
trans-trans-4'-ethoxybicyclohex-4-yl-trans-4-heptylcyclohexyl methyl ether
trans-trans-4'-propoxybicyclohex-4-yl-trans-4-ethylcyclohexyl methyl ether
trans-trans-4'-propoxybicyclohex-4-yl-trans-4-propylcyclohexyl methyl ether
trans-trans-4'-propoxybicyclohex-4-yl-trans-4-butylcyclohexyl methyl ether
trans-trans-4'-propoxybicyclohex-4-yl-trans-4-pentylcyclohexyl methyl ether
trans-trans-4'-propoxybicyclohex-4-yl-trans-4-heptylcyclohexyl methyl ether
trans-trans-4'-butoxybicyclohex-4-yl-trans-4-ethylcyclohexyl methy ether
trans-trans-4'-butoxybicyclohex-4-yl-trans-4-propylcyclohexyl methyl ether
trans-trans-4'-butoxybicyclohex-4-yl-trans-4-butylcyclohexyl methyl ether
trans-trans-4'-butoxybicyclohex-4-yl-trans-4-pentylcyclohexyl methyl ether
trans-trans-4'-butoxybicyclohex-4-yl-trans-4-heptylcyclohexyl methyl ether The following examples relate to liquid-crystalline phases according to the invention:

Example A

A liquid-crystalline phase consisting of
6% 2-p-cyanophenyl-5-butyl-1,3-dioxane,
6% 2-p-cyanophenyl-5-pentyl-1,3-dioxane,
5% 4-(trans-4-pentylcyclohexyl)-4'-(trans-4-propylcyclohexyl)biphenyl,
5% 4-(trans-4-pentylcyclohexyl)-4'-(trans-4-propylcyclohexyl)-2-fluorobiphenyl,
5% 4,4'-bis-(trans-4-pentylcyclohexyl)-2-fluorobiphenyl,
5% 2-p-pentyloxyphenyl-5-hexylpyrimidine
5% 2-p-hexyloxyphenyl-5-hexylpyrimidine
5% 2-p-heptyloxyphenyl-5-hexylpyrimidine
4% 2-p-nonyloxyphenyl-5-hexylpyrimidine 5% 2-p-heptyloxyphenyl-5-heptylpyrimidine
4% 2-p-nonyloxyphenyl-5-heptylpyrimidine
15% trans-1-p-propylphenyl-4-pentylcyclohexane
3% 1-(trans-4-propoxycyclohexyl)-2-(trans-4-propylcyclohexyl)ethane
13% trans,trans-4-propyl-4'-butyryloxybicyclohexane and
14% p-trans-4-propylcyclohexylphenyl butyrate has an optical anisotropy of 0.118.

Example B

A liquid-crystalline phase is prepared consisting of
34% r-1-cyano-cis-4-(trans-4-propylcyclohexyl)-1-heptylcyclohexane,
29% r-1-cyano-cis-4-(trans-4-pentylcyclohexyl)-1-heptylcyclohexane,
11% 1-(trans-4-methoxycyclohexyl)-2-(trans-4-propylcyclohexyl)ethane,
10% 1-(trans-4-ethoxycyclohexyl)-2-(trans-4-propylcyclohexyl)ethane,
4% trans-4-propylcyclohexyl trans,trans-4-propylcyclohexylcyclohexane-4'-carboxylate,
4% trans-4-pentylcyclohexyl trans,trans-4-propylcyclohexylcyclohexane-4'-carboxylate,
4% trans-4-propylcyclohexyl trans,trans-4-butylcyclohexylcyclohexane-4'-carboxylate and
4% trans-4-pentylcyclohexyl trans,trans-4-butylcyclohexylcyclohexane-4'-carboxylate.

Example C

A liquid-crystalline phase is prepared consisting of
20% r-1-cyano-cis-4-(trans-4-butylcyclohexyl)-1-pentylcyclohexane,
21% r-1-cyano-cis-4-(trans-4-pentylcyclohexyl)-1-octylcyclohexane,
11% 1-(trans-4-methoxycyclohexyl)-2-(trans-4-propylcyclohexyl)ethane,
10% 1-(trans-4-ethoxycyclohexyl)-2-(trans-4-propylcyclohexyl)ethane,
22% r-1-cyano-cis-4-(trans-4-pentylcyclohexyl)-1-(trans-4-heptylcyclohexyl)cyclohexane,
4% trans-4-propylcyclohexyl trans,trans-4-propylcyclohexylcyclohexane-4'-carboxylate,
4% trans-4-pentylcyclohexyl trans,trans-4-propylcyclohexylcyclohexane-4'-carboxylate,
4% trans-4-propylcyclohexyl trans,trans-4-butylcyclohexylcyclohexane-4'-carboxylate and
4% trans-4-pentylcyclohexyl trans,trans-4-butylcyclohexylcyclohexane-4'-carboxylate.

Example D

A liquid-crystalline phase is prepared consisting of
20% r-1-cyano-cis-4-(trans-4-propylcyclohexyl)-1-pentylcyclohexane,
21% r-1-cyano-cis4-(trans-4-butylcyclohexyl)-1-pentylcyclohexane,
11% 1-(trans-4-ethoxycyclohexyl)-2-(trans-4-propylcyclohexyl)ethane
10% 1-(trans-4-methoxycyclohexyl)-2-(trans-4-butylcyclohexyl)ethane,
22% 1-(trans-4-methoxycyclohexyl)-2-(trans-4-pentylcyclohexyl)ethane,
4% trans-4-propylcyclohexyl trans,trans-4-propylcyclohexylcyclohexane-4'-carboxylate,
4% trans-4-pentylcyclohexyl trans,trans-4-propylcyclohexylcyclohexane-4'-carboxylate,
4% trans-4-propylcyclohexyl trans,trans-4-butylcyclohexylcyclohexane-4'-carboxylate and
4% trans-4-pentylcyclohexyl trans,trans-4-butylcyclohexylcyclohexane-4'-carboxylate.

Example E

A liquid-crystalline phase is prepared consisting of
21% r-1-cyano-cis-4-(trans-4-propylcyclohexyl)-1-pentylcyclohexane,
23% r-1-cyano-cis-4-(trans-4-butylcyclohexyl)-1-pentylcyclohexane,
10% 1-(trans-4-ethoxycyclohexyl)-2-(trans-4-priopylcyclohexyl)ethane,
9% 1-(trans-4-methoxycyclohexyl)-2-(trans-4-butylcyclohexyl)ethane,
21% 1-(trans-4-methoxycyclohexyl)-2-(trans-4-pentylcyclohexyl)ethane,
4% trans-4-propylcyclohexyl trans,trans-4-propylcyclohexylcyclohexane-4'-carboxylate,
4% trans-4-pentylcyclohexyl trans,trans-4-propylcyclohexylcyclohexane-4'-carboxylate,
4% trans-4-propylcyclohexyl trans,trans-4-butylcyclohexylcyclohexane-4'-carboxylate,
4% trans-4-pentylcyclohexyl trans,trans-4-butylcyclohexylcyclohexane-4'-carboxylate.

Example F

A liquid-crystalline phase is prepared from
16% p-trans-4-propylcyclohexylbenzonitrile,
9% p-trans-4-butylcyclohexylbenzonitrile,
12% 1-(trans-4-propoxycyclohexyl)-2-(trans-4-propylcyclohexyl)ethane,
12% 1-(trans-4-methoxycyclohexyl)-2-(trans-4-pentylcyclohexyl)ethane,
12% 1-(trans-4-ethoxycyclohexyl)-2-(trans-4-pentylcyclohexyl)ethane,
9% trans-trans-4-propyl-4'-butyryloxybicyclohexane,
3% trans-4-propylcyclohexyl trans,trans-4-propylcyclohexylcyclohexane-4'-carboxylate,
3% trans-4-pentylcyclohexyl trans,trans-4-propylcyclohexylcyclohexane-4'-carboxylate,
3% trans-4-propylcyclohexyl trans,trans-4-butylcyclohexylcyclohexane-4'-carboxylate,
3% trans-4-pentylcyclohexyl trans,trans-4-butylcyclohexylcyclohexane-4'-carboxylate,
3% 4,4'-bis(trans-4-propylcyclohexyl)-2-fluorobiphenyl,
3% 4,4'-bis(trans-4-pentylcyclohexyl)-2-fluorobiphenyl,
3% 4,4'-bis(trans-4-propylcyclohexyl)biphenyl,
4% 4-(trans-4-pentylcyclohexyl)-4'-(trans-4-propylcyclohexyl)biphenyl and
5% 4-(trans-4-pentylcyclohexyl)-4'-(trans-4-propylcyclohexyl)-2-fluorobiphenyl.

Example G

A liquid-crystalline phase is prepared consisting of
6% 2-p-cyanophenyl-5-butyl-1,3-dioxane,
6% 2-p-cyanophenyl-5-pentyl-1,3-dioxane,
5% 4-(trans-4-pentylcyclohexyl)-4'-(trans-4-propylcyclohexyl)biphenyl,
5% 4-(trans-4-pentylcyclohexyl)-4'-(trans-4-propylcyclohexyl)-2-fluorobiphenyl,
5% 4,4'-bis(trans-4-pentylcyclohexyl)-2-fluorobiphenyl,
5% 2-p-pentyloxyphenyl-5-hexylpyrimidine,
5% 2-p-hexyloxyphenyl-5-hexylpyrimidine,
5% 2-p-heptyloxyphenyl-5-hexylpyrimidine,
4% 2-p-nonyloxyphenyl-5-hexylpyrimidine,
5% 2-p-heptyloxyphenyl-5-heptylpyrimidine,
4% 2-p-nonyloxyphenyl-5-heptylpyrimidine,
15% trans-1-p-propylphenyl-4-pentylcyclohexane, 6% 1-(trans-4-ethoxycyclohexyl)-2-(trans-4-pentycyclohexyl)ethane, 10% trans,trans-4-propyl-4'-butyryloxybicyclohexane and 14% p-trans-4-propylcyclohexylphenyl butyrate.

Example H

A liquid-crystalline phase is prepared consisting of

6% 2-p-cyanophenyl-5-butyl-1,3-dioxane,

6% 2-p-cyanophenyl-5-pentyl-1,3-dioxane,

5% 4-(trans-4-pentylcyclohexyl)-4'-(trans-4-propylcyclohexyl)biphenyl,

5% 4-(trans-4-pentylcyclohexyl)-4'-(trans-4-propylcyclohexyl)-2-fluorobiphenyl,

5% 4,4'-bis(trans-4-pentylcyclohexyl)-2-fluorobiphenyl,

5% 2-p-pentyloxyphenyl-5-hexylpyrimidine,

5% 2-p-hexyloxyphenyl-5-hexylpyrimidine,

5% 2-p-heptyloxyphenyl-5-hexylpyrimidine,

4% 2-p-nonyloxyphenyl-5-hexylpyrimidine,

5% 2-p-heptyloxyphenyl-5-heptylpyrimidine,

4% 2-p-nonyloxyphenyl-5-heptylpyrimidine,

15% trans-1-p-propylphenyl-4-pentylcyclohexane,

10% 1-(trans-4-ethoxycyclohexyl)-2-(trans-4-pentylcyclohexyl)ethane,

8% trans,trans-4-propyl-4'-butyryloxybicyclohexane and

12% p-trans-4-propylcyclohexylphenyl butyrate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclohexane derivative of the formula $$R^1-Cy-CH_2-Q-(Cy)_m-O-(CO)_n-CH_2-R^2$$

wherein $R^1$ is alkyl of 1 to 12 C atoms or alkyl of 1-12 C atoms wherein one or two non-adjacent CH groups are replaced by —O—, —O—CO— or —CO—O—, $R^1$ is H, alkyl of 1 to 12 C atoms or alkyl of 1-12 C atoms wherein one or two non-adjacent CH$_2$ groups are replaced by —O—, Cy is 1,4-cyclohexylene, Q is —CH$_2$—, m is 1 or 2, and n is 0 or 1.

2. A compound of claim 2, wherein all Cy groups are in trans-configuration.

3. A compound of claim 2, wherein $R^1$ and $R^2$ independently are alkyl or alkoxy.

4. A compound of claim 2, wherein $R^1$ and $R^2$ are of 2-10 C atoms and are straight chained.

5. A compound of claim 2, wherein n is 0 and both $R_1$ and $R_2$ are alkyl of 1 to 12 C atoms.

6. A compound of claim 2, wherein m is 1.

7. A compound of claim 2 of the formula n—alkyl—Cy—CH$_2$CH$_2$—Cy—n—alkoxy, wherein all alkyl portions are of 2-8 C atoms.

8. A compound of claim 2 of the formula n—alkyl—Cy—CH$_2$CH$_2$—Cy—n—alkanoyloxy, wherein all alkyl portions are of 2-8 C atoms.

9. A compound of claim 2 of the formula n—alkyl—Cy—CH$_2$CH$_2$—Cy—Cy—n—alkoxy, wherein all alkyl portions are of 2-8 C atoms.

10. A compound of claim 2 of the formula n—alkyl—Cy—CH$_2$CH$_2$—Cy—Cy—n—alkanoyloxy, wherein all alkyl portions are of 2-8 C atoms.

11. The compound of claim 8, which is 1-(trans-4-methyoxycyclohexyl)-2-(trans-4-pentylcyclohexyl)ethane.

12. In a liquid crystalline display element comprising a liquid-crystalline phase comprising at least two liquid-crystalline components, the improvement wherein at least one component is a compound of claim 1.

13. In a liquid-crystalline display element comprising a liquid-crystalline phase comprising at least two liquid-crystalline components, the improvement wherein at least one component is a compound of claim 2.

14. In an electrooptical display element comprising a liquid crystal dielectric a liquid-crystalline phase comprising at least two liquid-crystalline components, the improvement wherein at least one component is a compound of claim 2.

15. In a liquid-crystalline phase comprising at least two liquid-crystalline components, the improvement wherein at least one component is a compound of claim 1.

16. In a liquid-crystalline phase comprising at least two liquid-crystalline components, the improvement wherein at least one component is a compound of claim 2.

17. In a liquid-crystalline phase comprising at least two liquid-crystalline components, the improvement wherein at least one component is a compound of claim 3.

* * * * *